United States Patent
Feild et al.

(10) Patent No.: US 7,860,558 B2
(45) Date of Patent: Dec. 28, 2010

(54) ECG LEAD MISPLACEMENT DETECTION AND CORRECTION

(75) Inventors: Dirk Q. Feild, Simi Valley, CA (US); Richard E. Gregg, Westford, MA (US)

(73) Assignee: Koninklijke Philips Electronics N.V., Eindhoven (NL)

( * ) Notice: Subject to any disclaimer, the term of this patent is extended or adjusted under 35 U.S.C. 154(b) by 935 days.

(21) Appl. No.: 11/693,121

(22) Filed: Mar. 29, 2007

(65) Prior Publication Data

US 2007/0232946 A1 Oct. 4, 2007

Related U.S. Application Data

(60) Provisional application No. 60/787,827, filed on Mar. 31, 2006.

(51) Int. Cl.
*A61B 5/0402* (2006.01)

(52) U.S. Cl. .................................................. 600/509

(58) Field of Classification Search .......... 600/508–509
See application file for complete search history.

(56) References Cited

U.S. PATENT DOCUMENTS

| 3,757,778 | A * | 9/1973 | Graham .................. 600/508 |
| 4,850,370 | A | 7/1989 | Dower |
| 5,640,966 | A | 6/1997 | Heden et al. |
| 6,282,440 | B1 | 8/2001 | Brodnick et al. |
| 6,690,967 | B2 * | 2/2004 | Meij et al. .................. 600/509 |
| 6,751,493 | B2 * | 6/2004 | Wenger .................. 600/382 |
| 2002/0045837 | A1 * | 4/2002 | Wei et al. .................. 600/509 |
| 2005/0197586 | A1 * | 9/2005 | Pearlman .................. 600/509 |

OTHER PUBLICATIONS

"Intelligent Cardiac Telemonitoring System", Balazs et al., Computers in Cardiology 2004;31:748-748.*
Hedén, et al. "Detection of Frequency Overlooked Electrocardiographic Lead Reversals Using Artificial Neural Networks", ©1996 by Excerpta Medica, Inc. pp. 600-604 American Journal of Cardiology, vol. 78, Sep. 1, 1996 .
Hedén, et al. "Artificial Neural Networks for Recognition of Electrocardiogrpahic Lead Reversal", American Journal of Cardiology, 1995; 75:929-933.
Végsö, et al. "Electrode Reversal Detection in ECG Remote Monitoring", Measurement Science Review, vol. 5, Section 2, 2005 pp. 45-48.
Feild, et al., "Improved EASI Coefficients: Their Derivation, Values, and Performance", Journal of Electrocardiology, vol. 35, Supplement 2002, pp. 23-33.
Kors, et al., "Accurate Automatic Detection of Electrode Interchange in the Electrocardiogram" ©2001 by Excerpta Medica, Inc. pp. 396-399 American Journal of Cardiology, 2001; 88:396-399.

* cited by examiner

*Primary Examiner*—Carl H Layno
*Assistant Examiner*—Paula J Stice
(74) *Attorney, Agent, or Firm*—W. Brinton Yorks, Jr.

(57) ABSTRACT

A physiological parameter analysis system (10) detects ECG electrode wire misplacement. The system (10) includes a transformation component (32) that transforms original ECG information and combinations thereof from a first ECG lead system to a second ECG lead system and an inverse transformation component (34) that derives ECG information in the first ECG lead system from the transformed ECG information and the combinations thereof. The system (10) further includes an analysis component (38) that determines a correct ECG lead configuration in the first ECG lead system from among the original ECG information and the combinations thereof based on the derived ECG information.

15 Claims, 3 Drawing Sheets

ECG LEAD MISPLACEMENT DETECTION AND CORRECTION

CROSS REFERENCE TO RELATED APPLICATIONS

This application claims the benefit of U.S. provisional application Ser. No. 60/787,827 filed Mar. 31, 2006, which is incorporated herein by reference.

BACKGROUND

The following relates to systems and methods for processing physiological information. It finds particular application to detecting interchanged or misplaced ECG electrode wires from ECG information, and also contemplates correcting the ECG information.

An electrocardiogram (ECG or EKG) is a graphical representation of the electrical activity (e.g., electrical potentials/signals) of the heart used for applications such as screening and diagnosing cardiovascular disease. Such electrical activity is non-invasively measured by an electrocardiograph or other suitable electrical transducer, and the graphical representation is generated therefrom and/or by another device such as a computer. Conventional twelve lead (I, II, III, aVR, aVL, aVF, and $V_{1-6}$) electrocardiographs include ten electrodes for measuring the electrical activity of the heart. Each electrode is placed on the individual at a particular location within some tolerance. From these ten electrodes, twelve leads or potential differences are measured and/or derived. The leads record the average electrical activity generated by the summation of the action potentials of the heart at a particular moment in time. Other conventional systems include three, five, fifteen, sixteen, EASI, etc. lead systems.

FIG. 3 graphically illustrates an exemplary electrode placement in a standard twelve lead system. Leads I, II and III are measured over the limbs of the body. Lead I is measured from the right arm to the left arm; lead II is measured from the right arm to the left leg, and lead III is measured from the left arm to the left leg. From the average of the limb measurements, an imaginary point V located centrally in the chest above the heart is computed. The other nine leads are derived from potential differences between V and six precordial leads $V_{1-6}$ and three limb leads aVR, aVL and aVF are derived from combinations of leads I, II, and III. Each lead represents information from a different portion of the heart. The inferior leads (leads II, III and aVF) provide electrical activity reflective of the inferior wall of the heart, which is the apex of the left ventricle. The lateral leads (I, aVL, $V_5$ and $V_6$) provide electrical activity reflective of the lateral wall of the heart, which is the lateral wall of the left ventricle. The anterior leads, $V_2$ through $V_4$, represent the anterior wall of the heart, or the frontal wall of the left ventricle.

The quality of an ECG analysis depends on the placement of the electrodes and/or electrode lead wires. In addition, such placement is important because clinicians are trained to interpret ECG signals based on expected patterns. Such patterns typically are common to groups of individuals with the same disease state (e.g., no cardiac disease, ischemia, myocardial infarction, etc.). Ideally, the electrodes are placed at same anatomical locations on all patients. However, such constraints are unrealistic, if not impossible. Realistically, there is an acceptable margin of error for each electrode, and the margin may vary based on the device used to process the data and the clinician interpreting the resulting waveforms. Electrode misplacement includes any change of the electrodes and/or electrode wires outside their expected anatomical locations, including electrode wire reversal that involves interchanging of the electrode wires as they are supposed to be connected to the electrodes. Electrode wire reversal alters the shape of the graphical ECG wave. For example, it can make the electrical axis of the heart appear different from the true value.

It is postured in the literature that electrode wire reversal occurs on at least 2% of ECGs in a hospital population. Detection of a right arm—left arm interchange of wires is reliably performed using standard ECG criteria. However, detection of other electrode wire interchanges can be relatively difficult. One conventional approach to lead correction leverages the redundancy in the ECG signals to correct the reversal. With this approach, regression or other techniques are used to generate a model that predicts ECG lead signals by a linear combination of the other leads. If the predicted lead signal does not match the measured/derived lead signal, it is assumed that electrode wire reversal has occurred. All wire reversals are then applied to the ECG until the predicted lead signal matches the measured/derived lead signal. This approach can be time consuming and resource intensive.

BRIEF SUMMARY

In one aspect, a physiological parameter analysis system that detects ECG electrode wire misplacement is illustrated. The system includes a transformation component that transforms original ECG information and combinations thereof from a first ECG lead system to a second ECG lead system and an inverse transformation component that derives ECG information in the first ECG lead system from the transformed ECG information and the combinations thereof. The system further includes an analysis component that determines a correct ECG lead configuration in the first ECG lead system from among the original ECG information and the combinations thereof based on the derived ECG information.

One advantage includes detecting ECG electrode wire misplacement.

Another advantage resides in correcting ECG electrode wire misplacement.

Another advantage lies in identifying randomly placed electrodes.

Another advantage resides identifying the lead system used to process ECG information.

Still further advantages will become apparent to those of ordinary skill in the art upon reading and understanding the detailed description of the preferred embodiments.

BRIEF DESCRIPTION OF THE DRAWINGS

The drawings are only for purposes of illustrating embodiments and are not to be construed as limiting the claims.

DETAILED DESCRIPTION OF THE PREFERRED EMBODIMENTS

Figure 1:
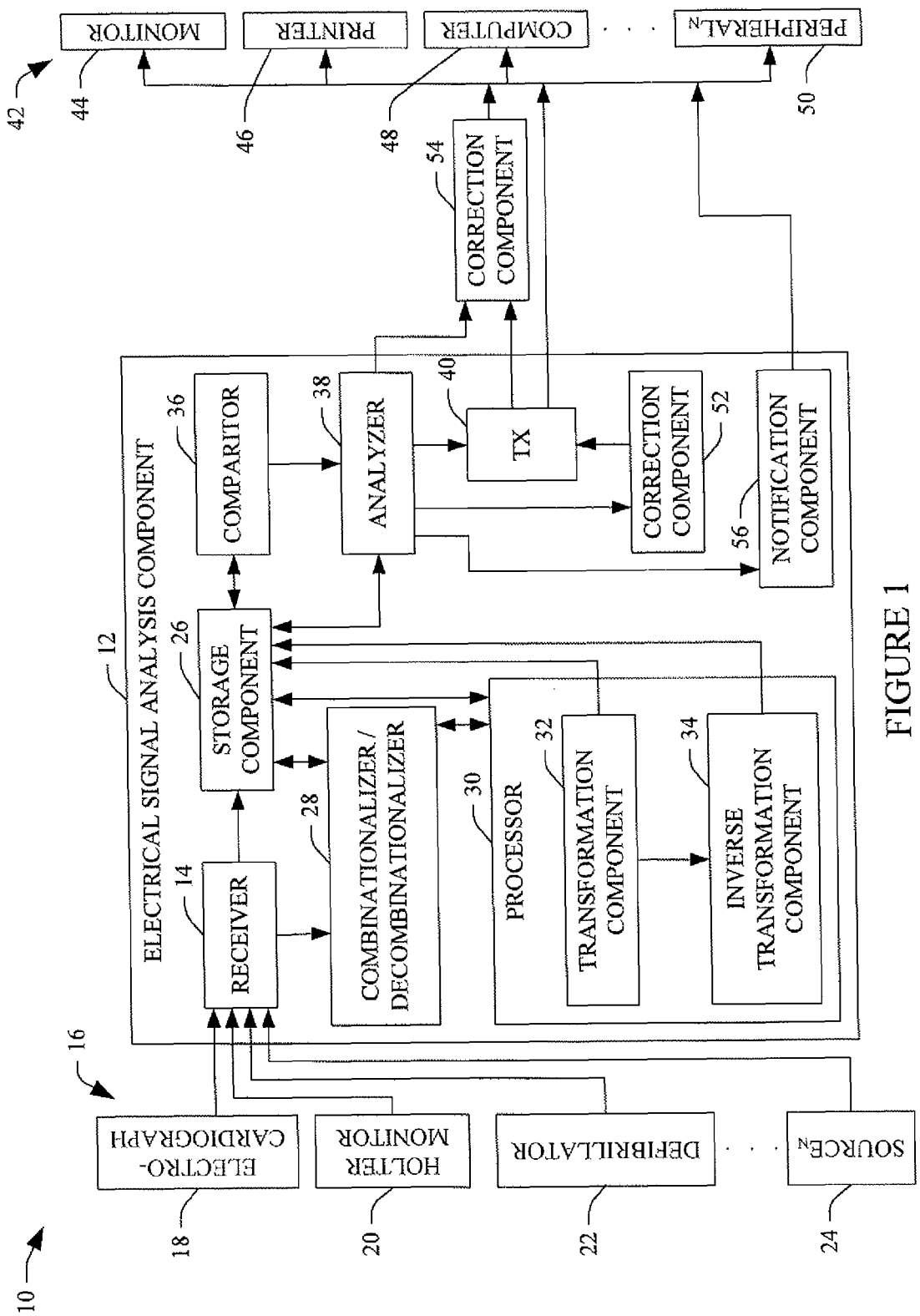
FIG. 1 illustrates a physiological parameter analysis system that detects ECG electrode misplacement from acquired ECG signals and optionally corrects the misplaced electrodes.

FIG. 1 illustrates a physiological parameter analysis system 10 (hereafter "system 10") that at least detects ECG electrode misplacement, including interchanged electrodes, from ECG signals. Optionally, the system 10 additionally corrects detected ECG electrode misplacement by determining which leads are reversed in the saved ECG data, swapping the lead signals, and re-calculating the ECG. The system 10 can also be used to identify electrodes (e.g., from randomly placed electrodes) and/or determine which lead system from a plurality of known lead systems has been used to process the ECG information.

The system 10 includes an electrical signal analysis component (ESAC) 12 having a receiver 14 that receives ECG information from N sources 16 (wherein N is positive integer). Examples of suitable sources include an electrocardiograph 18, a Holter monitor 20, a defibrillator 22, and other sources 24, including, but not limited to, a computer (not shown), a database (not shown), memory (not shown), an ECG monitor (not shown), etc. Such information includes individual electrode potentials with respect to a known reference such as signals corresponding to two or more of leads I, II, III, aVR, aVL, aVF, and $V_{1-6}$ from a conventional twelve lead system, leads I, II, III from a conventional three lead system, leads for five, fifteen, sixteen, etc. lead systems. The ESAC 12 can be a distinct component (stationary or mobile) and/or integrated with one or more of the sources 16. The conveyance of the ECG information from one or more of the sources 16 to the ESAC 12 can be through wired and/or wireless technologies associated with a bus, a backplane, a network, a cable, etc. Such conveyance can be initiated by either the ESAC 12 or the sources 16.

Upon receiving the ECG information, the receiver 14 stores the ECG information in a storage component 26 and/or provides the ECG information to a combinationalizer/decombinationalyzer 28. The storage component 26 can include various types of volatile and non-volatile memory, including various types of random access memory (RAM) and/or read only memory (ROM), static and/or portable memory, etc. The combinationalizer/decombinationalyzer 28 processes the ECG information and computes a number of combinations of the ECG information by selectively reversing leads. Each combination is representative of a possible correction for lead wire reversal and may or may not be the applicable correction. The combinationalyzer/decombinationalyzer 28 also inverts the combinations of the below discussed transformed ECG information.

Assuming the ECG information includes twelve lead ECG information, in one instance, the combinationalizer 28 generates10! combinations from the set of leads I, II, III, aVR, aVL, aVF, and $V_{1-6}$ (from the 10 lead wires). In another instance, the set of leads is first delineated into logical subsets. For example, the leads can be separated into a group corresponding to short lead-wires (e.g., $V_1$-$V_6$) and a group corresponding to long lead-wires (e.g., I, II, III, aVR, aVL, and aVF) since reversing a long-wire and short-wire lead would be very obvious to the operator. Through such grouping, the number of combinations for two lead switches, three lead rotations, etc. is reduced to about seventeen thousand. Other criteria can also be used to further reduce the number of combinations and/or result in a different set of combinations. Regardless of whether all possible combinations or some subset thereof is used, the computation time via a standard computing system is sub-second, for example, in a range of hundredths of a second or less.

The original ECG information and the combinations are stored in the storage component 26 and/or provided to a processor 30 for further processing. In one instance, the original ECG information and each combination is separately processed by the processor 30. In another instance, the original ECG information and each combination are processed by the processor 30 in parallel. For example, the original ECG information and the combinations thereof can be stored in a matrix or other data structure. The data can then be concurrently provided to the processor 30 via the matrix or other data structure. Using a matrix, reversal of the leads can be achieved relatively effortlessly and computationally efficiently (e.g., in about $1/100^{th}$ of a second) by simply shifting columns of the transformation matrix.

The processor 30 processes, in series and/or parallel, the ECG information and the combinations with a transformation component 32 that transforms the original ECG information and the combinations, to any known lead system (usually one with reduced redundancy). For example, U.S. Pat. No. 4,850,370 shows a transform from a standard twelve lead system, to the EASI lead system. Other transforms, variations thereof and/or other lead systems are also contemplated. The resulting ECG information is stored in the storage component 26 and/or conveyed to an inverse transformation component 34, which applies an inverse transform to the transform of component 32. Next this result is further transformed by the inverse combination that was originally applied (e.g. if V1 and V6 were swapped then they are swapped back and if V1-V2-V3 were right rotated then they are left rotated to undo the operation). This will derive or reconstruct a waveform very similar to the original ECG information from the EASI transformed ECG information (assuming that the original ECG had the lead misplacement corresponding to the combination applied). The resulting derived ECG information is stored in the storage component 26 and/or provided to a comparator 36.

Additionally or alternatively, each combination can be computed in isolation and only the comparison code saved in the storage component 26. In this embodiment, one sample of the 12-lead ECG can be represented as an eight element vector (typically two of leads I, II, and III plus leads V1 through V6), which can be incorporated into a matrix, Each lead swap can then be represented as an 8×8 matrix. The lead swap inverse matrices are the same, but other inverse matrices are different (e.g., a right rotate of leads has a left rotate as an inverse). A final array is then computed as a function of the following: (ECG array)×(lead swap matrix)×(12 lead to EASI lead matrix)×(EASI lead to 12 lead matrix)×(inverse lead swap matrix). This information is also stored in the storage component 26 and/or provided to a comparator 36. It is to be appreciated that these matrices can be pre-combined.

The following provides a brief description of the known EASI lead system and transformations between the EASI lead system and other lead systems such as the standard twelve lead ECG system. The transformation is based on the dipole hypothesis underlying vectorcardiography. Under this assumption, the electrical activity of the heart can be represented by a single dipole (the heart vector), and corrected orthogonal vectorcardiographic systems can directly record three orthogonal time-varying components X, Y, and Z of the heart vector and display them either as scalar ECG tracings or as a vectorcardiographic loop in three dimensions.

The difference between any corrected vectorcardiographic lead system and the EASI lead system is that the former yields the orthogonal components of the heart vector directly, whereas the latter records three non-orthogonal leads and produces all other leads (including the orthogonal leads and the twelve lead ECG) by an analog network or by algebraic calculations performed digitally. This difference notwithstanding, both vectorcardiography and EASI-electrocardiography, rely on the same dipole hypothesis. Under the fundamental assumption of the dipole hypothesis, the EASI lead system, as well as any vectorcardiographic system, can be extended to yield other desired leads, provided that the goodness-of-fit measures between the actual and derived leads are acceptable. The lead transformations from EASI leads to other leads produces an estimate, not an exact replica, of the desired lead. The differences between the estimated ECG signals and those of the actual desired lead can be measured quantitatively and objectively assessed.

Figure 4:
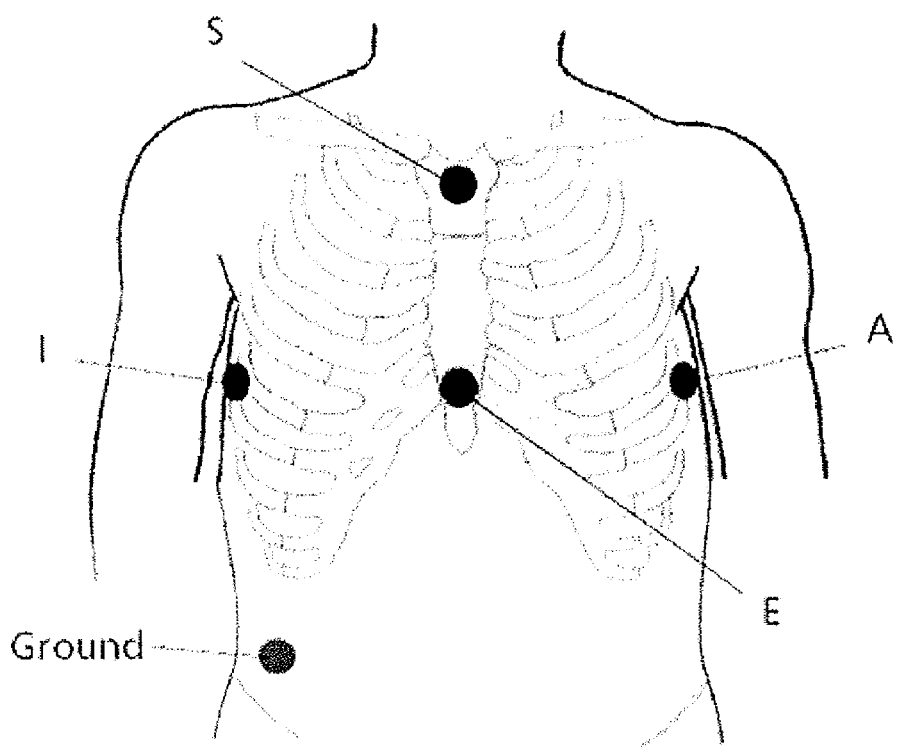
FIG. 4 graphically illustrates electrode placement for the EASI ECG system.

Under the assumption that the electrical activity of the heart can be represented by a single dipole (the dipole hypothesis) and that the human body is approximately a linear volume conductor, properties of a lead can be represented by a lead vector. Lead vectors associated with a plurality of body-surface locations can be used directly to derive lead transformations. The following basis vectors represent one suitable relationship between the non-orthogonal basis vectors $\overline{C}$ associated with bipolar leads ES, AS, and AI of the EASI lead system (electrode placement for this lead system is graphically illustrated in FIG. 4) and the orthogonal leads X, Y, and Z:

$C_{ES} = -0.63\,i + 0.29\,j - 1.75\,k;$ $C_{AS} = 0.99\,i + 0.46\,j + 0.17\,k;$ and $C_{AI} = 1.42\,i - 0.18\,j + 0.11\,k,$ where i, j, and k are unit vectors in the direction of the x, y, and z axes. The coefficients have units of impedance [$\Omega$/m].

Under the assumption of the fixed-location single dipole source with orthogonal vector components px i, py j, and pz k, the lead voltages in the three bipolar EASI leads can be calculated as scalar products of a moment p of the dipole and the appropriate lead vector c:

$V_{ES} = -0.63\,px + 0.29\,py - 1.75\,pz;$ $V_{AS} = 0.99\,px + 0.46\,py + 0.17\,pz;$ and $V_{AI} = 1.42\,px - 0.18\,py + 0.11\,pz,$ in which the coefficients still have units of impedance. These represent three simultaneous linear algebraic equations in three unknowns: px, py, and pz. A solution of this system in terms of known lead voltages (V) is the following:

$p_x = 0.06\,V_{ES} + 0.20\,V_{AS} + 0.59\,V_{AI};$ $p_y = 0.09\,V_{ES} + 1.68\,V_{AS} - 1.13\,V_{AI};$ and $p_z = -0.57\,V_{ES} + 0.21\,V_{AS} + 0.40\,V_{AI},$ in which the coefficients have units of admittance.

From the foregoing, a scalar product for a specific lead of interest (e.g., $V_1$, $V_2$, $V_3$, etc.) with a dipole moment in terms of three lead voltages in leads ES, AS, and AI (e.g., a linear combinations thereof) in which the coefficients are dimensionless can be obtained.

Alternatively, a statistical approach, under the assumptions of the dipole hypothesis and the linearity of the volume conductor, in which the time-varying lead voltage of any desired lead is a linear combination of the time-varying voltages recorded in three reference leads can be used. Using voltages from the bipolar leads ES, AS, and AI of the EASI lead system as reference voltages, the voltage $V_i$ of any arbitrary lead i is a linear combination of the voltages in leads ES, AS, and AI:

$V_i = \alpha_i\,V_{ES} + \beta_i\,V_{AS} + \gamma_i\,V_{AI}.$

This linear equation can be represented in terms of the constant dimensionless coefficient triplet ($\alpha_i$, $\beta_i$, $\gamma_i$). The unknown values of the coefficients $\alpha_i$, $\beta_i$, and $\gamma_i$ can be determined by fitting them to the measured sets of voltages $V_i$, $V_{ES}$, $V_{AS}$, and $V_{AI}$.

Returning to FIG. 1, the comparator 36 compares the original twelve or other ECG information with the derived ECG information generated via the inverse transformation and undoing of combination in component 34 and/or the final array with the original array. The comparison is provided to an analyzer 38, which analyzes the data.

The analyzer 38 analyzes the differences between the final array and the original array. The final score is a single number which is saved in the storage component 26. The "best" score (e.g., using the identity matrix) is typically considered the "best" choice. Additionally or alternatively, the analyzer 38 analyzes the differences between the original ECG signals and each combination of the derived ECG information and determines, based on the difference, whether the original ECG information and/or any combination corresponds to correct electrode placement or misplaced electrodes. For instance, a relatively small difference typically corresponds to a correctly formed ECG; whereas, lead-wire reversal results in a relatively larger difference. The original ECG information and combinations thereof are then categorized accordingly. That is, if the original uncorrected set of leads is associated with the smallest difference, the original ECG information is deemed to be correct and without electrode wire reversal. However, if a corrected version of the original ECG information (one of the combinations) is associated with the smallest difference, then the original ECG information is deemed incorrect and the electrode wire configuration of this combination is deemed correct.

If the original ECG information is deemed correct, the original ECG information is conveyed by a transmitter (TX) 40 to one or more destination devices 42, including a monitor 44, a printer 46, a computer 48, and other peripherals devices 50, such as a plotter (not shown), a cardiac monitoring station (not shown), central electronic storage (not shown), etc. However, if the original ECG information is deemed incorrect, the ECG information is conveyed to one of an optional internal correction component 52 and an external correction component 54 (which can be a separate component or integrated with one or more of the destination devices 42). The optional internal correction component 52 suitably reverses lead-wire ECG information to generate corrected ECG information. The corrected ECG information is then provided to the transmitter 40 and conveyed to one or more of the destination devices 42. This correction is performed without physically reversing the leads and acquiring a new set of measurements. The correction can also be performed on previous ECG information that is stored, for example, upon later determining that the previously acquired data was subject to electrode reversal. In addition, the correction can be automatically or manually invoked. The external correction component 54 can also suitably reverse the lead-wire ECG information to generate corrected ECG information and convey the corrected ECG information to one or more of the destination devices 42. Likewise, the correction can be automatically or manually invoked.

Similar to receiving ECG information, conveyance to ECG information from the ESAC 12 to correction component 54 and/or one or more of the destination devices 42 is through wired and/or wireless technologies associated with a bus, a backplane, a network, a cable, etc., and can be initiated by either the ESAC 12 or the correction component 54 and/or one or more of the destination devices 42.

The analyzer 38 communicates with a notification component 56. Such communication includes data about the ECG information analyzed, such as whether the original ECG information is deemed correct, whether a lead-wire has been misplaced, which lead-wired was misplaced, whether a correction was performed on-board or through the external correction component 54, etc. The notification component 56, in response, transmits various notifications. For example, in one instance the notification component 56 provides an audio and/or visual alarm and/or an indication of the reversal and/or the correction. In another instance, the notification component 56 sends a message to an email address, a cell phone, a conventional telephone, a pager, a personal data assistant (PDA), a central monitoring station, a bedside monitor, a satellite, the computer 48, the central storage, etc. Such message may invoke further alarms and/or include information about the ECG information, the subject patient, the operator who obtained the data, the location of the patient, etc.

As another alternate embodiment, the operator can randomly place electrodes at suitable locations and the present concept can be used to determine which lead is which. Analogously, there are currently about twenty standard lead systems in use. This technique can tell which of the lead systems has been used and select the appropriate signal processing software for that lead system. Further, the technique can also determine which lead system was used and if any leads were reversed. In another embodiment, if the original and derived ECG information match within pre-selected limits, processing the various permutations of the combinations is omitted. In another embodiment, if the original and derived ECG information for all permutations of lead combinations fail to match within the pre-selected limits, then a message is sent that one of the electrodes is mis-positioned and one or more electrodes should be re-applied to the patient.

Figure 2:
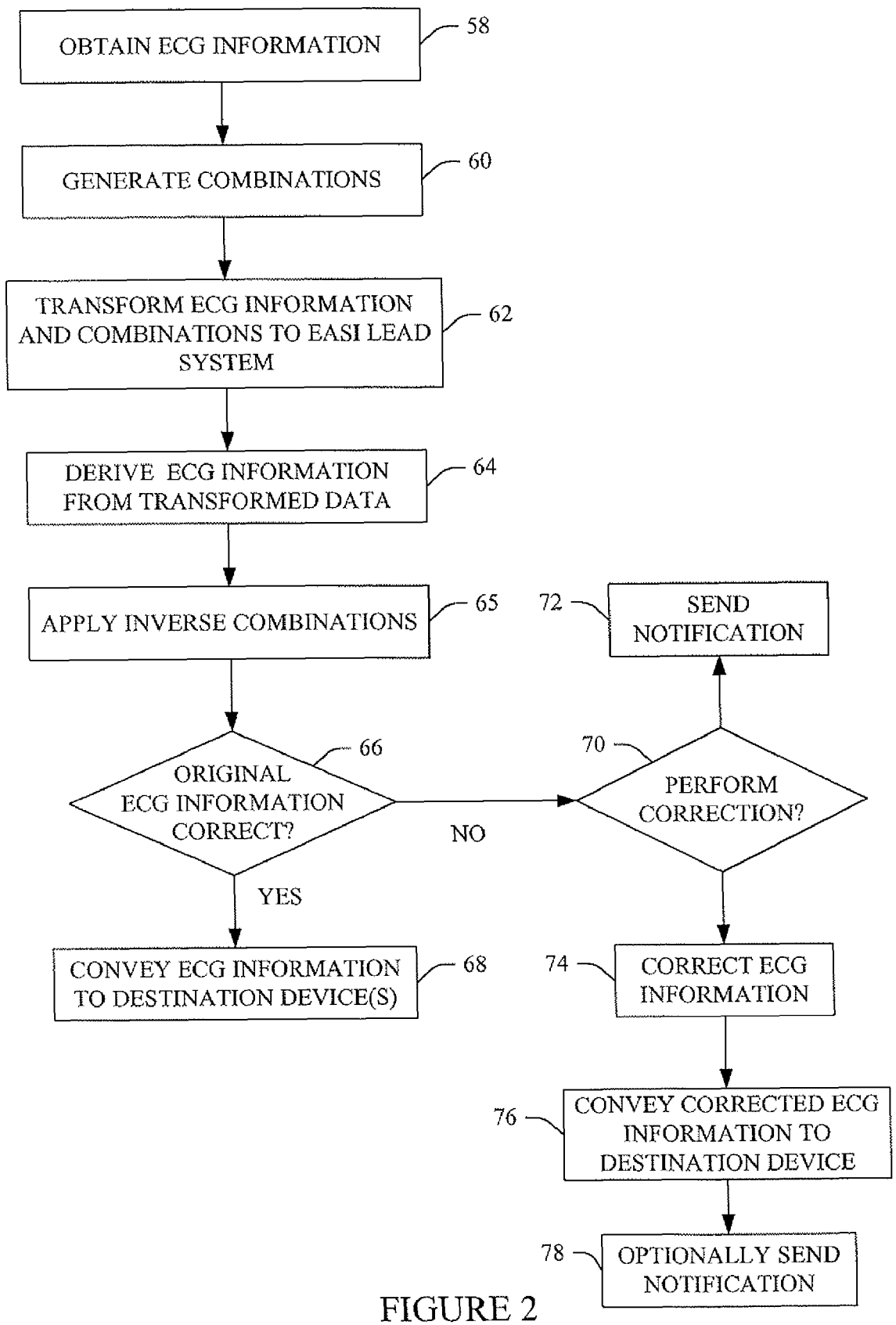
FIG. 2 illustrates a method that detects ECG electrode misplacement from acquired ECG signals and optionally corrects the misplaced electrodes.
Figure 3:
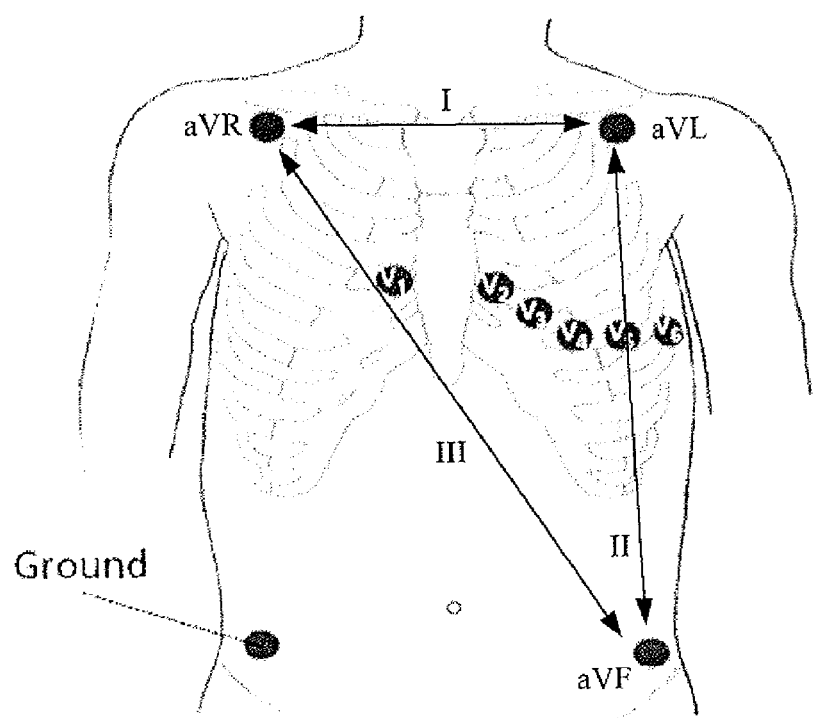
FIG. 3 graphically illustrates electrode placement for a standard twelve lead ECG system.

FIG. 2 illustrates a method that detects ECG electrode misplacement from acquired ECG signals and optionally corrects the data for the misplaced electrodes. At reference numeral 58, ECG information is obtained. For example, the ECG information can be obtained by the system 10. In another example, the ECG information can be obtained by an electrocardiograph, a Holter monitor, a defibrillator, an electronic patient file, and/or other source. The information can be obtained directly from such source and through an intermediary device such as a computer, a database, memory, an ECG monitor, etc. As discussed above, the ECG information can be associated with a three, five, twelve, fifteen, sixteen, etc. lead system. For instance, the ECG information can include lead I, II, III, aVR, aVL, aVF, and $V_{1-6}$ data from a conventional twelve lead system.

At 60, the ECG information is processed to generate a plurality of combinations by selectively reversing leads. Each combination is representative of a possible correction for lead wire reversal and may or may not be the applicable correction. In one instance, the combinations represent all possible permutations. In another instance, various criteria is used to reduce the number of combinations. For example, the leads can be separated into two or more groups, including, but not limited to, a group corresponding to short lead-wires (e.g., $V_1$-$V_6$) and a group corresponding to long lead-wires (e.g., I, II, III, aVR, aVL, and aVF). Such grouping corresponds to an obvious lead misplacement by an operator. These particular grouping reduce the number of combinations to about one hundred combinations. In either instance, the computation time via a standard computing system is sub-second. The resulting data can be provided for further processing via a serially or parallel technique such as via a matrix or other data structure.

At 62, the ECG information is transformed in series and/or parallel to the EASI lead system and/or variations thereof and/or other lead systems. This can be achieved via matrix multiplication and/or otherwise. The resulting transformed FCC information is then used to derive, via an inverse matrix and/or other technique, the original lead system at 64. For instance, ECG information represented in the EASI lead system can be used to generate ECG information in the standard 12-lead system. At 65, the inverse combinations are applied. At 66, the original ECG information and combinations and the derived ECG information is compared and the difference therebetween is analyzed to determine whether the original ECG information is correct. If the original uncorrected set of leads is associated with the smallest difference, the original ECG information is deemed to be correct and without electrode wire reversal. At 68, original ECG information deemed correct is provided to one or more destination devices, including an ECG monitor, a printer, a computer, a plotter, a cardiac monitoring station, electronic patient file, etc.

However, if one of the combinations (a corrected version of the original ECG information) is associated with the smallest difference, then the original ECG information is deemed to include an electrode wire reversal and the electrode wire configuration of this combination is deemed correct. This categorization reflects that a relatively small difference corresponds to a correctly formed ECG; whereas, a relatively larger difference corresponds to electrode wire misplacement. At 70, it is determined whether the ECG information will be corrected. If not, then at 72 a notification indicating that the ECG information includes a misplaced electrode wire is presented to an operator. Such communication can involve sending a message to an email address, a cell phone, a conventional telephone, a pager, a personal data assistant (PDA), a central monitoring station, a bedside monitor, a satellite, monitor or screen on the ECG device, etc. Additionally or alternatively, such message may invoke one or more alarms and/or include information about the ECG information, the subject patient, the operator who obtained the data, the location of the patient, etc.

If it is determined at 70 that the ECG information will be corrected, then at 74, an automatic and/or manually invoked correction can be performed to render corrected ECG information. Such correction can include suitably reversing electrode information via a computer or the like. This can be achieved without performing further measurements and can be applied to previously saved ECG information. At 76, the corrected ECG information is provided to one or more destination devices. At 78, a notification and/or message including information such as an indication that the original ECG information was deemed correct and that a electrode wire was misplaced, which electrode wire was misplaced, the correction that was performed, etc. is optionally transmitted. This message may also invoke alarms and/or include information about the ECG information, the subject patient, the operator who obtained the data, the location of the patient, etc.

The invention has been described with reference to the preferred embodiments. Modifications and alterations may occur to others upon reading and understanding the preceding detailed description. It is intended that the invention be constructed as including all such modifications and alterations insofar as they come within the scope of the appended claims or the equivalents thereof.

The invention claimed is:

1. A physiological parameter analysis system (10) that detects ECG electrode wire misplacement, comprising:
   a receiver for receiving original ECG information corresponding to a plurality of electrode leads in a first lead system;
   a combinationalyzer/decombinationalyzer (28) that is operatively connected to the receiver and that generates one or more combinations from the original ECG information, each combination representing a permutation of the received electrode leads;
   a processor that is operatively connected to the combinationalyzer/decombinationalyzer, the processor having;
      a transformation component (32) that transforms the original ECG information and each combination from a first lead system to a second lead system different from the first lead system; and
      an inverse transformation component (34) that reverse transforms the transformed original ECG information and each combination from the second lead system to the first lead system;
   a comparator (36), operatively connected to the combinationalyzer/decombinationalyzer and the inverse transformation component, which computes a difference between the original ECG information and the reverse transformed original ECG information, and which computes a difference between each combination and each reverse transformed combination;
   an analyzer (38), operatively connected to the comparator, that determines a misplaced electrode wire in the original ECG information based on the computed differences; and
   a notification component (56), operatively connected to the analyzer, that transmits a notification of the analyzer determination.

2. The system (10) as set forth in claim 1, wherein the first lead system is one of a three, five, twelve, fifteen, and sixteen lead ECG system.

3. The system (10) as set forth in claim 1, wherein the second lead system is an EASI ECG lead system.

4. The system (10) as set forth in claim 1, wherein the notification comprises an alarm based on the analyzer determination of the misplaced electrode wire in the original ECG information.

5. The system (10) as set forth in claim 1, wherein the notification includes a message sent to at least one of an email address, a cell phone, a conventional telephone, a pager, a personal data assistant (PDA), a central monitoring station, a bedside monitor, a satellite, a viewing screen, an alarm light, and a network.

6. The system (10) as set forth in claim 5, wherein the notification includes information about the original ECG information, a subject patient, an operator who obtained the data, and a location of the patient.

7. The system (10) as set forth in claim 1, further including:
   a correction component (52, 54), operatively connected to the analyzer, that automatically corrects the original ECG information based on the analyzer determination of the misplaced electrode wire in the original ECG information.

8. The system (10) as set forth in claim 7, wherein the notification component (56) transmits a message indicating that the original ECG information included the misplaced electrode wire, which electrode wire was misplaced, and the correction that was performed.

9. The system (10) as set forth in claim 1, wherein the receiver (14) receives the ECG information from a source device (16), the source device (16) including one or more of an electrocardiograph (18), a Holter monitor (20), a computer, a defibrillator (22), a database, memory, and an ECG monitor.

10. A method that detects ECG electrode misplacement, comprising the steps of;
    receiving first ECG information corresponding to a plurality of electrode leads associated with a first lead system;
    generating additional ECG information from the first ECG information by computationally reversing a pair of electrode leads from the plurality of electrode leads;
    transforming the first ECG information and the additional ECG information to a second lead system that is different from the first lead system;
    reverse transforming the transformed first and additional ECG information in the second lead system back to the first lead system in order to generate reverse transformed first ECG information and reverse transformed additional ECG information;
    comparing the reverse transformed first ECG information to the received first ECG information, and comparing the reverse transformed additional ECG information to the generated additional ECG information;
    analyzing differences between the comparing the reverse transformed first ECG information to the received first ECG information data and the comparing the reverse transformed additional ECG information to the generated additional ECG information data; and
    determining whether a one of the received first and additional generated ECG information comprises correctly placed electrode leads based on the analyzing step.

11. The method as set forth in claim 10, wherein the determining step includes:
    selecting one of said first ECG information or additional ECG information as having correctly placed electrode leads based on the smaller of the differences.

12. The method as set forth in claim 10, further including:
    automatically correcting the received first ECG information when it is determined that the additional generated ECG information comprises correctly placed electrode leads.

13. The method as set forth in claim 10, further including:
    transmitting a notification of a misplaced electrode wire when the additional generated ECG information comprises correctly placed electrode leads.

14. The method as set forth in claim 10, wherein the second lead system is an EASI ECG lead system.

15. A computer processor or software programmed to perform the method of claim 10.

* * * * *